Feb. 3, 1942. B. D. DRAIN Plant Pat. 502

STRAWBERRY PLANT

Filed Sept. 14, 1940

Inventor

Brooks D. Drain

By Cameron, Kerkam & Sutton Attorneys

Patented Feb. 3, 1942

Plant Pat. 502

UNITED STATES PATENT OFFICE

502

STRAWBERRY PLANT

Brooks D. Drain, Knoxville, Tenn., assignor to The University of Tennessee Research Corporation, Knoxville, Tenn., a corporation of Tennessee Application September 14, 1940, Serial No. 356,850

1 Claim. (Cl. 47—62)

This invention relates to the asexual reproduction of berry plants, and more particularly to a new and distinct variety of strawberry produced by artificial pollination of the Missionary plant with pollen of the Howard (sometimes designated Premier) strawberry.

The object of the invention is to produce a novel variety of strawberry plant which will develop a relatively large number of runner plants, be more or less resistant to foliage diseases, root rot and fruit rots, and produce a fruit, red throughout, of high flavor and good size, and which will possess the desirable characteristics of the fruit and plant of the parent varieties.

Figure 1:
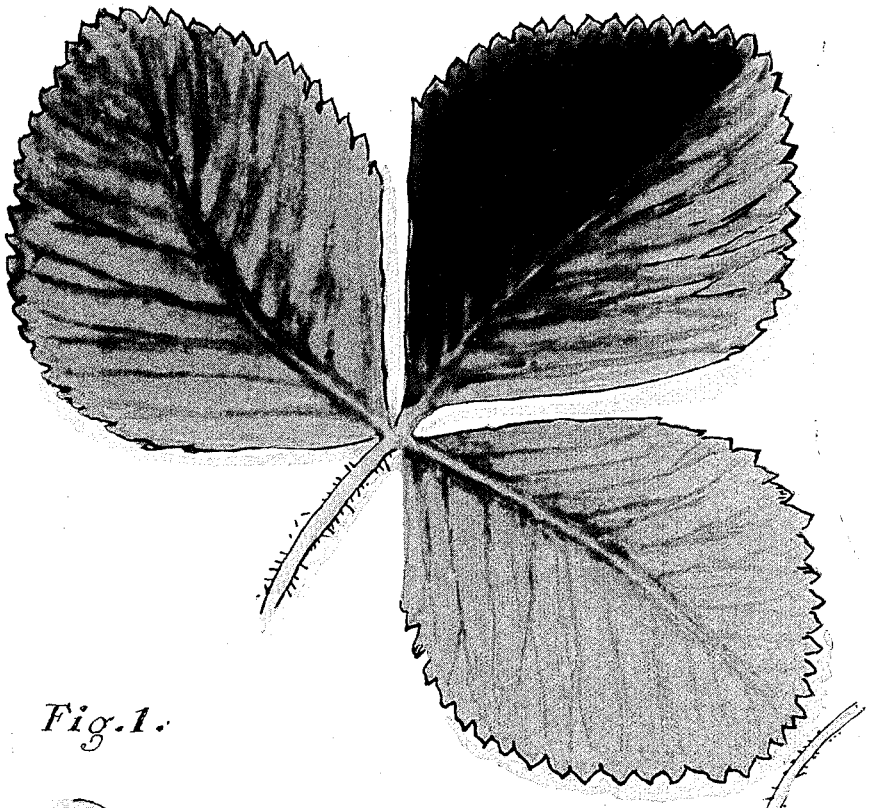
Figure 2:
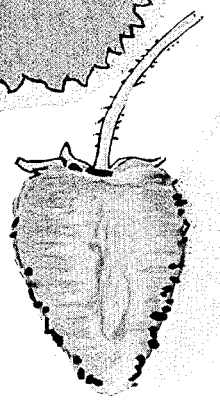
Figure 3:
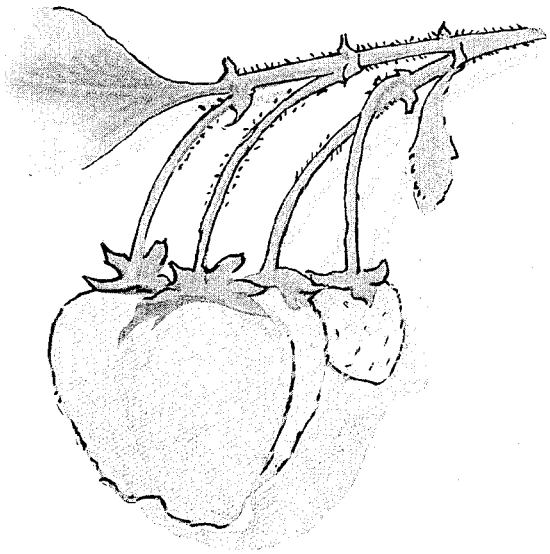

In the accompanying drawing, Fig. 1 is a view of a leaf of the plant of the present invention showing its color and other characteristics, Fig. 2 is a longitudinal section of one of the berries of the new plant showing its internal color and characteristics, and Fig. 3 is a view of a fruiting stem of said plant showing both ripe and green berries.

In producing the plant of the present invention, the pollen of Howard strawberry was placed in the blossoms of Missionary plants, after first removing the pollen producing parts from the blossoms of the latter variety. The pollinated blossoms were then protected so that they could not receive pollen from any other plant, and were allowed to develop into fruit. The seeds from the latter fruit were then planted and permitted to sprout, and after the plants had grown to sufficient size, they were transplanted and allowed to fruit in the field. At about the time when they were fruiting in the field, each plant and its vegetatively developed runner plants were examined for freedom from insects and diseases, and for desirable growth habits. The fruit was also tasted and examined for desirable fruit characteristics. The best among a large number of seedlings was then selected and saved, and propagated asexually using runner plants to produce the plant of the present invention. All the plants which are now growing, including that from which the accompanying drawing was made, have come from this original seedling.

The new variety of strawberry is particularly adapted to the soil and climate of the eastern and western sections of the State of Tennessee.

The new variety of strawberry differs from its parent varieties in numerous respects. As to the Missionary strawberry, the leaves of the Missionary are a lighter green in color and appear thinner than the leaves of the Tennessee Supreme. The fruit of Tennessee Supreme is round conic while that of the Missionary is blunt conic and frequently necked in shape. The fruit of Tennessee Supreme is medium red and glossy and that of the Missionary is a very dark dull red. The flesh is subacid and highly flavored while that of the Missionary is quite tart and not of the highest flavor. The new variety thrives and produces excellent crops in the soil and climate of the State of Tennessee while the Missionary is considered poorly adapted to this soil and climate.

As to the Howard variety, the Tennessee Supreme produces more numerous runners than the Howard and this results in larger yields of fruit per acre. The leaves of the new variety are medium green and those of the Howard are usually dark green. The seeds of the new variety tend to be even with the surface of the fruit while those of the Howard are sunken in the fruit. The Howard variety has not grown well in the eastern and western parts of Tennessee whereas the new variety is well adapted to the soil and climate of these sections and has given large yields therein.

One vigorous mother plant of the new variety will produce from a few to more than one hundred runner plants, depending upon soil fertility and growing conditions, and large crops of medium red berries will be produced in early midseason. The foliage of the plant is dense, the leaves being medium to large in size with long, medium thick petioles. Although a slight amount of leaf blight has developed on the foliage, no leaf scorch has been noted to date, nor has any root rot been observed.

The berries produced by this plant are medium to large in size, round conic to wedged in shape, and smoothly formed, and have seeds about even with the surface of the berry. The surface of the berry is glossy and evenly colored a medium red, while the flesh is solid, juicy, medium firm and also a medium red in color. The fruit is subacid, well flavored, and medium firm.

Other characteristics of the plant of the present invention are as follows:

Plants: Numerous. Vigorous. Tall. Productive. Spring bearing.

Susceptibility:

*Insects.*—Weevil.

*Diseases.*—Some blight.

Runners: Slender with long internodes.

Leaves: Medium size. Light green. Rugose. Glossy.

Petiole: Medium thickness.
Flowers: Perfect.

*Date of bloom.*—April 9 to May 7, 1941, at Jackson, Tennessee.

*Length of blooming season.*—April 9 to May 7, 1941, at Jackson, Tennessee.

*Size.*—diameter—$1\frac{1}{16}$ inches. Medium size.

*Petals.*—Number—5. Medium size.

*Stamens.*—Medium in number.

*Receptacle.*—Medium size.

*Fruit-stems.*—Medium length. Slender. Semi-erect.

*Pedicels.*—Medium length. Medium thickness.

*Fruit*

Season: Early.
Date of Ripening: May 2 to May 22, 1941, at Jackson, Tennessee.
Length of Season: 20 days at Jackson, Tennessee.
Picking Quality: Good.
Shipping Quality: Medium. Medium size. Drops in size. Uniform. Regular. Conic, sometimes wedged.
Apex: Obtuse.
Surface Color: Medium red. Glossy. Attractive. Colors evenly.
Calyx: Medium size. Raised. *Color*—light green. Adherence to fruit—Medium.
Sepals: Long. Medium breadth.
Seeds: Medium in number. Sunken.
Flesh: Medium red. Juicy. Medium firmness. Subacid. High-flavored.
Quality: Best.
Use: Dessert, kitchen, frozen pack. Market, home.
Desirability: A quality variety for nearby markets and the frozen-pack package trade.

*Remarks.*—The fruit is very high-flavored and bright red to the center. The plants are healthy and drought resistant under Tennessee conditions.

What is claimed is:

A healthy, prolific fruiting strawberry plant variety substantially as illustrated and described, characterized by subacid, well flavored fruits which are medium red throughout, and by the development of a large number of runner plants.

BROOKS D. DRAIN.